United States Patent [19]

Meyer

[11] 4,117,022
[45] Sep. 26, 1978

[54] NICKEL BIS-DIORGANO-ORTHOPHOSPHATES THEIR PREPARATION AND USE

[75] Inventor: Jeffrey G. Meyer, Adrian, Mich.

[73] Assignee: Anderson Development Company, Adrian, Mich.

[21] Appl. No.: 839,117

[22] Filed: Oct. 3, 1977

Related U.S. Application Data

[60] Division of Ser. No. 630,323, Nov. 10, 1975, which is a continuation-in-part of Ser. No. 416,390, Nov. 16, 1973, abandoned.

[51] Int. Cl.$^2$ .................................................. C07C 3/21
[52] U.S. Cl. ...................... 260/669 P; 260/683.15 D
[58] Field of Search .................... 260/683.15 D, 669 P

[56] References Cited

U.S. PATENT DOCUMENTS

| | | | |
|---|---|---|---|
| 3,390,201 | 6/1968 | Drew | 260/683.15 D |
| 3,467,726 | 9/1969 | Griffin | 260/683.15 D |
| 3,689,588 | 9/1972 | Dunn | 260/683.15 D |
| 3,949,013 | 4/1976 | Yoo et al. | 260/683.15 D |
| 4,052,473 | 10/1977 | Yagi et al. | 260/669 P |
| 4,055,582 | 10/1977 | Fahey | 260/683.15 D |

Primary Examiner—C. Davis
Attorney, Agent, or Firm—Browdy and Neimark

[57] ABSTRACT

This invention comprises novel organic-solvent-soluble nickel bis-diorgano-orthophosphates and their preparation by the reaction of certain simple salts or esters of divalent nickel with certain non-aromatic triorgano orthophosphates free of aliphatic unsaturation and separation of the novel compounds. The simple salts or esters include preferably the halides, nitrates and acetates of divalent nickel.

This invention further comprises the use of these novel compounds, preferably in solution, as catalysts. When used in conjunction with alkyl aluminum halides, controlled oligomerization of ethylene, propylene and other olefins is achieved with the formation of polymers with low degrees of polymerization, e.g. 2 to 10, preferably no more than about 6 mers. When certain vanadium catalysts are added to these combined catalysts, high polymers of such monomers are achieved with significant residual aliphatic unsaturation.

8 Claims, No Drawings

NICKEL BIS-DIORGANO-ORTHOPHOSPHATES THEIR PREPARATION AND USE

CROSS REFERENCE TO RELATED APPLICATION

This is a division, of application Ser. No. 630,323 filed Nov. 10, 1975 which is CIP Appl. of Ser. No. 416,390 filed Nov. 16, 1973 now abandoned.

BACKGROUND OF THE INVENTION

A number of systems have been devised for the preparation of numerous types of organophosphorus compounds containing at least one other type of metal. Some of these systems are illustrated in U.S. Pat. Nos. 2,228,659; 2,370,080; 2,488,662; 2,885,417; 3,055,925; 3,065,065; 3,231,347; 3,275,668; 3,297,573; 3,334,978; 3,354,189 and 3,412,182 and United Kingdom Specification No. 1,135,261. These systems generally employ solvents and/or phosphorus compounds containing at least one acidic hydrogen atom.

A system employing triorgano-orthophosphates and anhydrous nickel dichloride is shown in an article by Paul et al. in Indian Journal of Chemistry, 10, (4), pages 447-8, 1972. However, the products of this system are complex crystalline compounds which are insoluble in all the common organic solvents and which are consequently not well suited for olefin polymerization systems. These products apparently crystallize out of the system so that while the anhydrous nickel dichloride starting material is soluble in the triorgano-orthophosphate starting material, there is no evidence that the complex products are soluble even in the triorgano-orthophosphate starting material.

It is a principal object of this invention to provide a novel class of nickel organophosphorus compounds and novel methods of preparing such organophosphorus compounds and novel methods of preparing such organophosphorus compounds. It is a further object of this invention to provide a method for preparing nickel organophosphorus compounds soluble in organic solvents from known salts and organic orthophosphates.

Nickel organophosphorus compounds have been used alone and with cocatalysts for the controlled polymerization of olefins as shown, for example, in U.S. Pat. Nos. 3,432,518; 3,655,810 and 3,660,445.

Another object of this invention is to provide new catalyst combinations for controlled oligomerization both alone and during high polymerization of olefins with other catalysts.

SUMMARY OF THE INVENTION

This invention comprises novel compounds which are soluble in organic solvents and which have the general formula:

$$Ni[OP(O)(OR)_2]_2$$

in which each R is a monovalent non-aromatic hydrocarbon group free of aliphatic unsaturation, i.e. an alkyl or cycloalkyl group, containing one to eight, preferably two to four, carbon atoms or a non-aromatic hydrocarbon ether group free of aliphatic unsaturation, i.e. an alkoxyalkyl group, containing three to six carbon atoms or a chlorinated or brominated derivative of any of such groups.

The novel compounds of this invention are preferably prepared by (1) mixing an organic phosphate of the formula $(O)P(OR)_3$ in which each R is as defined above with a nickel compound, preferably hydrated, of the formula $M_aZ_b$ in which each M is divalent nickel, each Z is a non-reducing substituent, $a$ is 1 or 3, $b$ is 1 or 2 and the values of $a$ and $b$ depend on the valence of Z, (2) heating the mixed components at a temperature between about 0° and 250° C., preferably 100° to 200° C., and at a pressure and for a time sufficient to cause a reaction between them to produce a product of this invention and (3) separating the desired product from the reaction mixture.

This invention also comprises a combination catalyst for controlled olefin oligomerization consisting essentially of the reaction product of (A) a nickel bis-diorgano-orthophosphate of the general formula $Ni[OP(O)(OR)_2]_2$ in which each R is as defined above and (B) and alkyl aluminum halide of the general formula $R'_c Al X_d$ in which each R' is an alkyl group of one to six carbon atoms, each X is a halogen atom, preferably chlorine or bromine, each of $c$ and $d$ is 1 or 2 and the total of $c$ and $d$ is 3. The mol ratio of (A) to (B) can range from 1:1 to 1:20 but is preferably in the range of 1:8 to 1:12.

This invention further comprises a combination catalyst for olefin polymerization consisting essentially of components (A) and (B) as described above in the ratio range described together with (C) a vanadium bis-diorgano-orthophosphate of the general formula $V(O)[OP(O)(OR)_2]_2$ in which each R is as defined above, mol ratio of (C) to (B) ranging from 1:4 to 1:10.

This invention further comprises the use of the above described catalyst combinations in a method for olefin oligomerization of polymerization consisting essentially of (1) mixing the appropriate catalyst combination described above with (D) a monoor di-olefin which can be any aliphatic, cycloaliphatic or aromatic hydrocarbon containing no more than about 8 carbon atoms, preferably an aliphatic hydrocarbon containing no more than about 4 carbon atoms and/or a styrene, either along or with (E) a hydrocarbon solvent free of aliphatic unsaturation, i.e., an alkyl, cycloalkyl or aromatic hydrocarbon containing up to 14 carbon atoms, any aromatic hydrocarbon being optionally substituted with up to about four lower alkyl groups or other non-interfering substituents such as, for example, amines, oxygen-free anions of non-metallic inorganic acids such as chlorine atoms and bromine atoms and nitrile groups, at a temperature and pressure and for a time sufficient to cause reaction of (D) and (2) separating the resulting products. The total amount of catalyst combination is present in an amount of from about 0.0001 to 0.01 total mol per mol of (D). This system operates spontaneously as an exothermic reaction as soon as the components are mixed. Generally, the system temperature can range from 0° to 250° C., preferably 50° to 150° C., and the system pressure can range from 1 to 500 psig., preferably 10 to 100 psig. The desired reaction can take up to 24 hours, but for the aliphatic olefins the reaction is generally almost instantaneous and is maintained by a continuous addition of monomer or monomers with or without additional catlayst.

DESCRIPTION OF THE PREFERRED EMBODIMENTS

The reaction for the preparation of the novel organic-solvent-soluble compounds of this invention follows the general course:

$$(O)P(OR)_3 + M_aZ_b \rightarrow M[OP(O)(OR)_2]_2 + RZ$$

Each R can be, for example, any alkyl, alkoxyalkyl or cycloalkyl group of up to about eight carbon atoms. Specific examples of such groups include methyl, ethyl, propyl, isopropyl, butyl, isobutyl, tert-butyl, pentyl, isopentyl, hexyl, isohexyl, 2,2,4-trimethylpentyl, 2-methylpentyl, 2,2-dimethylbutyl, 2,3-dimethylbutyl, heptyl, 2-methylhexyl, 3-methylhexyl, 3,3-dimethylpentyl, octyl, 2,3-dimethylhexyl, 2,4-dimethylhexyl, 2-ethylhexyl, 2-ethylbutyl, methoxyethyl, ethoxyethyl, butoxyethyl, cyclohexyl, cyclobutyl and cyclopentyl groups and chlorinated and brominated derivatives such as the 3-chloropropyl, chlorocyclohexyl and 2,3-dibromopropyl groups.

Typical examples of the organic phosphates which can be used in this method are triorgano orthophosphates such as trimethyl orthophosphate, triethyl orthophosphate, tributyl orthophosphate, dimethyl amyl orthophosphate, diethyl amyl orthophosphate, isopropyl di-isoamyl orthophosphate, tri-tertiary-butyl orthophosphate, tri-n-amyl orthophosphate, tri-isoamyl orthophosphate, trihexyl orthophosphate, ethyl dihexyl orthophosphate, tri-2-ethylhexy orthophosphate, tri-n-octyl orthophosphate, tri-2-ethoxyethyl orthophosphate, dimethyl n-octyl orthophosphate, diethyl n-octyl orthophosphate, di-n-propyl n-octyl orthophosphate, isopropyl isoamyl isooctyl orthophosphate, tricyclohexyl orthophosphate, tricycloheptyl orthophosphate, diethylcyclobutyl orthophosphate and chloropropyl di-isopropyl orthophosphate.

The reaction conditions for the preferred preparation of the novel compounds of this invention can vary considerably, but the temperature range is generally from about 0° C. to about 250° C., preferably about 100° C. to about 200° C. The temperatures which can be used depend primarily on the stability of the products and the solubility of the reactants. The absolute pressure of the reaction system can range from about 0.01 to about 1.5 atmospheres, depending on the boiling points and/or vapor pressures of the reactants, products and solvent medium, but usually the pressure of the system is at least about 0.5 atmosphere. The reaction time is generally at least about 20 minutes or 0.3 hour and no more than about 24 hours with a range of 1 to 3 hours being preferred.

The nickel compounds used in the methods of this invention for the preparation of the novel nickel bis-diorgano orthophosphates of this invention are all well known in the art. They can be best defined as selected from the group consisting of nickel salts of non-reducing non-metallic inorganic acids and carboxylic acids containing up to about 18 carbon atoms and metal hydroxides, the metal being limited to divalent nickel. They can also be described as compounds of the general formula $M_aZ_b$, in which each M is a divalent nickel atom. The Z substituent must be non-reducing and can be an anion of a non-metallic inorganic acid, such as the chlorate, bromite, fluorosilicate, chloride, bromide, iodide, fluoride, nitrate, nitrite, perchlorate, silicate, sulfate and bisulfate anions or their respective hydrates, a hydroxyl group or an organic carboxylic group containing from one to about 18 carbon atoms, peferably in the form of an aliphatic hydrocarbon as in a fatty acid residue. The preferable Z substituents are halogen atoms, the nitrate group, the sulfate group and fatty aicd residues of no more than about six carbon atoms. While free water should not be present, the compounds $M_aZ_b$ are preferably hydrated.

While any of the above-described types of Z substituents can be attached to M atoms, it is most preferable that each substituent is a chlorine atom, a nitrate group or a low molecular weight organic carboxylic group, preferably the acetate group. This preference is based on economic practicality, first, with regard to the cost of the reactant $M_aZ_b$ and, second, with regard to the separation of the product from the reaction mixture. While the techniques for separation of chemicals from any type of system have become very sophisticated, it is preferable that starting components are selected so that the desired product and the by-product automatically separate at ambient temperatures and pressures. Thus, in the preferred method, if the desired product $Ni[OP(O)(OR)_2]_2$ is soluble in the reaction medium, it is preferable that any liberated water of hydration and the by-product RZ is readily distillable from the system. Consequently, the choice of reactants is usually governed by a simple determination of the easiest way of producing and separating the desired product, but it need not be.

Purification of the desired product immediately after preparation is critical for insuring the form of material useful as a catalyst component. Particularly important is removal of free water and polar organic impurities which can cause extraneous undesirable reaction with the nickel product $Ni[OP(O)(OR)_2]_2$.

Addition of drying agents, such as molecular sieves, or chemical scavengers, such as metal hydrides, to solutions containing the monomeric or oligomeric product is particularly suitable for this purpose.

Examples of desired products include:

Nickel bis(dipropyl orthophosphate), nickel bis(di-n-octyl orthosphoshate), nickel bis(di-4,4-dimethylhexyl orthophosphate), nickel bis(di-2-ethylhexyl orthopyosphate), nickel bis(diethyl orthophosphate), nickel bis(diisobutyl orthophosphate), nickel bis(monobutyl mono-tert-butyl orthophosphate), nickel bis(monopentyl mono-2-methylpentyl orthophosphate), nickel bis(di-3-methylhexyl orthophosphate), nickel bis(mono-2-ethylhexyl mono-3-methylhexyl orthophosphate), nickel bis(di-2,3-dimethylhexyl orthophosphate), nickel bis(dicyclohexyl orthophosphate), nickel bis(dibutyl orthophoshate), nickelmono(diethyl orthophosphate) mono(diisohexyl orthophosphate), nickel bis(di-3,3-dimethylpentyl orthophosphate), nickel mono(monoheptyl monohexyl orthophosphate) mono(monoheptyl monooctyl orthophosphate), nickel bis(di-2,2,4-trimethylpentyl orthophosphate), nickel bis(di-2-ethosyethyl orthophosphate), nickel bis(dicyclopentyl orthophosphate), nickel bis(di-2,2-dimethylbutyl orthophosphate), nickel mono(monopropyl monobutyl orthophosphate), mono(monoamyl monohexyl orthophosphate), nickel bis (dicyclohexyl orthophosphate), nickel bis(dicyclobutyl orthophosphate), nickel bis(di-3-chloropropyl orthophosphate), nickel bis(bis-2,3-dibromopropyl orthophosphate) and nickel bis(di-2-chloroethyl orthophosphate).

The organic-solvent-soluble nickel bis-diorgano-orthophosphates of this invention are particularly useful in combination with alkyl aluminum halides as a catalyst system for controlled olefin oligomerization. More specifically, this catalyst system consists essentially of the reaction product of (A) one or more nickel bis-diorgano-orthophosphates of the formula $Ni[OP(O)(OR)_2]_2$ as described above and (B) one or more alkyl aluminum halides of the general formula $R'_cAlX_d$ in which each R' is an alkyl group of one to about six carbon atoms, each x is a halogen atom, preferably chlorine or bromine, each of c and d is 1 or 2 and the total of c and d is 3, the mol ratio of (A) to (B) being in the range of 1:1 to 1:20, preferably 1:8 to 1:12. Generally, as the mol ratio of (A) to (B) increases, the average degree of polymerization of the resulting oligomer increases.

The alkyl aluminum halides are primarily the compounds $R'Al X_2$, $R'_2 Al X$ and mixtures thereof including the mixtures of the formula $R'_3Al_2X_3$ usually referred to as the sesquihalides. Each $R'$ can be, for example, a methyl, ethyl, propyl, iso-propyl, n-butyl, sec-butyl, tert-butyl, pentyl or hexyl group. Each X can be fluorine, chlorine, bromine or iodine. Examples of suitable alkyl aluminum halides include diethylaluminum chloride, n-butylaluminum dibromide, ethyl aluminum sesquichloride, methyl aluminum sesquichloride, ethyl aluminum sesquibromide, ethyl aluminum sesquifluoride and the like.

The catalyst combination of (A) and (B) can be further augmented with an additional cocatalyst (C) one or more vanadium bis-diorgano-orthophosphates of the formula $V(O)[OP(O)(OR)_2]_2$ as described above. Examples of such compounds (C) correspond directly to the examples of the corresponding nickel compounds set forth above except that a vanadium atom with an oxygen atom is substituted for the nickel atom in each compound. Such catalyst combinations of (A), (B) and (C) combine the oligomerizing properties of the novel nickel compounds with the known high polymerization properties of the vanadium compound. When component (C) is included, it should be present in a mol ratio to component (B) in the range of 1:4 to 1:10.

The catalyst compositions of (A) and (B) or of (A), (B) and (C) are simply prepared by mixing the components. The components can be mixed prior to addition to the polymerization reaction system or can be added simultaneously or separately to such reaction system. The desired reaction generally takes place immediately, but in any case it is known that the desired reaction takes place in no more than two hours.

The combination catalyst system is used in the method comprising (1) mixing the appropriate combination catalyst described above with (D) one or more mono-or di-olefins which can be any aliphatic, cycloaliphatic or aromatic hydrocarbons containing no more than about 8 carbon atoms, preferably styrene and/or one or more aliphatic hydrocarbons containing no more than about 4 carbon atoms, alone or with (E) a hydrocarbon solvent free of aliphatic unsaturation selected from the class aromatic hydrocarbon being optionally substituted with up to about four lower alkyl groups or other non-interfering substituents such as amines, anions of non-metallic inorganic acids and nitrile groups, at a temperature and pressure and for a time sufficient to cause the reaction of (D) and (2) separating the resulting product.

Examples of suitable olefins (D) include ethylene, propylene, isobutylene, butene-1, cis-butene-2, trans-butene-2, pentene-1, hexene-1, cyclopentene, cyclohexene, cycloheptene, 4-methylcyclooctene, 2-methylbutene-1, styrene, butadiene, isoprene, 3-vinylcyclohexene and the acyclic and cyclic terpenes. Substitution or inclusion of non-interfering groups as in acrylonitrile, methyl vinyl ether, vinyl chloride and chloroprene is not intended to put such olefins outside the scope of suitable olefins (D). The preferred olefins are styrene and aliphatic olefins of 2 to 4 carbon atoms.

For these polymerization reactions the reacting monomer or monomers may act as a solvent for the system. Alternatively, an inert solvent (E) can be employed. While simple paraffin oils, cycloaliphatic hydrocarbons and aromatic hydrocarbons can be used, the halogenoalkanes are preferred, particularly methylene chloride, chloroform, carbon tetrachloride and ethylene chloride.

The mol ratio of total catalysts to (D) can be as little as 0.0001:1 as taught in the prior art but preferably ranges from 0.001:1 to 0.01 to 1.

For the polymerization of olefins (D) no solvent component (E) need be present, but a small amount of component (E) may accelerate the polymerization reaction. In such cases the mol ratio of (E) to (D) should be less than 0.01:1, preferably no more than about 0.001:1.

The temperatures required for the oligomerization and polymerization reactions with the catalyst combinations of this invention are not particularly critical with the catalyst combinations of this invention. Some heat may be necessary to initiate reaction such as heating to at least 30° C. The maximum temperature which can be employed is dependent on the melting points, boiling points and decomposition points of the catalytic components, the reacting component (D) and the products as well as the desired control over rate of reaction. For practical purposes, the maximum temperature is about 200° C. and the preferred temperature range is 40° C. to 100° C.

Ambient pressures are satisfactory generally ranging from atmospheric pressure to no more than about 50 atmospheres, preferably no more than 100 psig.

Under these conditions of temperatures and pressure the oligomerization and polymerization reactions can be operated batchwise for from five minutes to four hours or more or these reactions can be run continually. The separation of the desired product is well within the skill of the art being primarily a problem of fractional distillation.

Typically, for either oligomerization or polymerization a reaction vessel is purged with some monomer (D) if gaseous or an inert gas such as nitrogen. Then enough of the alkyl aluminum halide (B) is added to dry the vessel. An inert solvent such as heptane may be added. The desired amount of components (A) and (B) and (C), if any, are added, preferably in (A) to (B) mol ratios of 1:8 to 1:12 and (B) to (C) mol ratios of 4:1 to 10:1, with monomer (D) at ambient pressure at a sufficient rate to allow continuous reaction but not at such an excessive rates as to kill the reaction. The product is then distilled off if oligomer or extracted if high polymer. Although prior addition of cocatalyst (B) favors rapid initiation and more rapid reaction of monomer (D) in the presence of the initial excess of this component (B), concurrent addition of (B) with (A), with or without (C), favors formation of higher molecular weight oligomer products. Generally, this latter method is preferred for the catalyst combination of (A), (B) and (C).

The following examples are illustrative of the best presently-known methods of practicing this invention and are not intended to limit this invention the scope of which is delineated in the appended claims. Unless otherwise stated, all quantitative measurements are by weight.

EXAMPLE I

Preparation of Nickel Bis-Dibutylorthophosphate

Nickel dichloride hexahydrate $NiCl_2 \cdot 6H_2O$ (50.4 grams; 0.21 mole) was oven-dried at 200° F. for 40 hours to 34.5 grams of a yellow-brown solid. This solid was mixed with 120.0 grams of tri-n-butylorthophosphate (0.45 mole) and heated over a period of 2 hours to 190° C. During the resulting reaction 5.0 grams of water and 38.0 grams of butyl chloride (0.41 mole) were distilled off. The remaining product cooled to a yellow-brown syrup soluble in benzene, hexane and chloroform. Upon prolonged standing, a yellow solid crystallized from the syrup showing that the desired product nickel bis-dibutylorthophosphate was in fact present in the form of a highly concentrated solution in the excess tri-n-butylorthophosphate plus minute amounts of any by-products.

About 10 grams of the raw yellow crystalline solids in syrup was mixed with 20 ml. of petroleum ether. The solids were allowed to settle, and the supernatant liquid was decanted. This procedure was repeated twice more with the solids. The washed solids were dried by evaporating the remaining petroleum ether in vacuo at room temperature leaving about 5 grams of yellow waxy solids. This purified nickel bis-dibutylorthophosphate was found to be readily soluble in benzene forming a golden yellow solution. The solid was also soluble in chlorinated and polar solvents but tended to form a green gel.

Organic-solvent-soluble nickel bis-diethylorthophosphate can be prepared using the same general technique.

EXAMPLE II

Oligomerization of Ethylene

To a two-liter stirred autoclave, after having been purged with ethylene, was added 500 ml. of benzene, 2.0 grams of ethyl aluminum sesquichloride EASC (0.0162 mole calculated as one aluminum atom per mole) and sufficient ethylene on a continuous basis to maintain a pressure of 50 psig in the autoclave. To this system was immediately added 5 ml. of a solution of 0.75 gram of the syrupy product of Example I in 15 ml. of benzene, and the reaction temperature in the autoclave rose from 26° C. to 42° C. Additional 5 ml. portions of the catalyst solution were added 30 and 60 minutes respectively after the first catalyst addition to give a total of 0.00157 mole of catalyst. The flow of ethylene was increased to maintain the system pressure at 100 psig. The reaction was allowed to proceed for 3 hours at ambient temperature (about 50° C.) after which the autoclave was vented. The total ethylene added amounted to 30.4 moles.

The 1293 grams of remaining liquid was fractionally distilled to separate three fractions in addition to the benzene solvent. The first fraction was 550 grams of a liquid boiling in the range of 40° to 70° C., having a refractive index of 1.4190 and being made up of oligomers of which a major constituent was cis-2-butene as indentified by infrared spectrum. The section fraction was 125 grams of a liquid boiling in the range of 92° to 130° C., having a refractive index of 1.4315 and being made up of oligomers having degrees of polymerization primarily in the range of 3 to 6. The third fraction was 75 grams of liquid boiling above 130° C. and having a refractive index of 1.4338. Thus, of the 750 grams of fractionated product 90 percent was made up of oligomers as described above instead of high polymers.

Similar polymerizations have been run using nickel bis-diethylorthophosphate instead of the nickel bis-dibutylorthophosphate resulting in products having in one case 86% oligomers having degrees of polymerization of 3 to 4, over 87% being trimers, and in a third case 97% being trimers and the remainder being tetramers. No basis for this variation has been proven.

EXAMPLE III

Oligomerization of Ethylene to Heavier Products

The reaction of Example II was repeated, except without the initial addition of ethyl aluminum sesquichloride to the autoclave. The same nickel catalyst and aluminum cocatalyst amounts were added uniformly and concurrently during the first 45 minutes of reaction. The reaction temperature in the autoclave rose from 24° C. to 50° C. within 5 minutes after the initial catalyst and cocatalyst additions, and the reaction was maintained at 50° C. by cooling for the remainder of the reaction period. The flow of ethylene was adjusted to maintain 100 psig. After 1 hour about 80 grams of ethylene (2.8 moles) had been consumed by the reaction, and the autoclave was vented.

The product was distilled to recover 74 grams of high boiling liquid, which gas chromatography analyzed to consist more than 90° of hexamers to decamers of ethylene. The refractive index of this fraction at 25° C. was 1.4720.

EXAMPLE IV

Oligomerization of Propylene

The catalyst and cocatalyst for this run were prepared by dissolving 0.75 gram of the syrupy product of Example 1 in 15 ml. of chloroform and 1.5 grams of ethyl aluminum sesquichloride in 15 ml. of heptane to give 0.00157 mole of the nickel catalyst and 0.0121 mole of the EASC calculated as one aluminum atom per mole.

A two liter stirred autoclave was purged with propylene and pressurized to 20 psig after which 550 ml. of n-heptane was introduced. Then 5 ml. each of the catalyst and cocatalyst solutions were added followed by 200 ml. of propylene monomer. The resulting reaction raised the ambient temperature to 40° C. The reaction was maintained continuously for a period of two hours at 50 psig and 40° C. by regularly adding catalyst, cocatalyst and propylene monomer until all of the catalyst and cocatalyst solutions and 2000 ml. of additional propylene monomer had been added to give a total of 28.8 moles of monomer. The autoclave was then vented to atmospheric pressure.

The product was fractionally distilled to give three distinct fractions in addition to the solvent. The first fraction was 760 grams of a liquid boiling in the range of 61° to 91° C., having a refractive index of 1.3900 and being made up of oligomers of which a major portion was a combination of methyl pentenes and methyl cyclopentane as identified by infrared spectra. The second fraction was 170 grams of a liquid boiling in the range of 130° to 140° C., having a refractive index of 1.4165 and being made up of oligomers having degrees of polymerization primarily in the range of 3 to 6. The third fraction was 125 grams of a liquid boiling above 140° C. and having a refractive index of 1.4397. Thus, of the 1055 grams of fractionated product over 88 percent was made up of oligomers as described above.

A similar polymerization using nickel bis-diethylorthophosphate instead of nickel bis-dibutylorthophosphate resulted in a product containing 49.4% dimers and 30.6% trimers, but no basis has been proven for this variation.

EXAMPLE V

Copolymerization of Ethylene and Propylene

A stirred two liter autoclave with controlled cooling coils was purged and then pressurized to 30 psig with ethylene gas. Hydrogen gas was then added until the pressure rose to 34 psig. Subsequently, 1300 ml. of dry, pure n-heptane was added followed by 320 ml. of liquid propylene. A reservoir containing an equimolar mixture of ethylene and propylene was coupled to the autoclave, and the mixture was introduced at a rate sufficient to maintain a pressure of 60 psig throughout the copolymerization reaction to give a total of 3.5 moles of monomer.

A combination catalyst was prepared by dissolving 0.31 gram of vanadium bis-diethylorthophosphate (0.00083 mole) and 0.19 gram of nickel bis-dibutylorthophosphate (0.00040 mole) in 30 ml. of benzene. The cocatalyst was 2.4 grams of ethyl aluminum sesquichloride (0.020 as calculated above) dissolved in 30 ml. of n-heptane.

The combination catalyst and cocatalyst solutions were added concurrently and continuously to the reaction mixture for a period of 80 minutes after initiation, the temperatures being maintained in the range of 20° to 30° C. Upon completion of the reaction and removal of solvent 123 grams of clear polymer gum product was isolated.

The above preparation was then repeated omitting the nickel bis-dibutylorthophosphate to produce another polymer gum product.

Both products were examined and found to be ethylene-propylene copolymers. However, the proton magnetic resonance (60 Mhz NMR) spectra of the products showed that the first product contained olefinic bond structures which were absent in the second polymer product. This finding was verified by the infrared spectra of cast films of the products, the first product having significant absorption around 900 cm.$^{-1}$. Vapor bromination of the film of nickel-catalyzed polymer appreciably increased absorption around 1600 cm.$^{-1}$, indicating bromine replacement of the olefinic hydrogens without any significant saturation of the olefinic bond structures.

Oxidation of the films on glass in air at 200° F. for several hours resulted in curing of the nickel-catalyzed film no less gummy texture than the other polymer. Adhesion of the nickel catalyzed polymer to glass was appreciably greater than the other polymer.

EXAMPLE VI

Oligomerization of Isobutylene

A stirred two liter autoclave with cooling controlled to maintain below 50° C. was purged and then pressurized to 30 psig. with isobutylene gas. Subsequently 500 ml. dry, pure benzene solvent was added, and a reservoir of isobutylene was connected to the autoclave to maintain 30 psig. throughout the reaction.

Catalyst containing 0.50 grams nickel bis-dibutylorthophosphate (0.00105 mole) and cocatalyst containing 2.0 grams ethyl aluminum sesquichloride (0.0162 mole) in separate solvents (80 cc. total) were metered uniformly and concurrently into the autoclave over a period of two hours. Heat evolved by the oligomerization raised the reaction temperature from 25° C. to 50° C. after the initial addition of catalyst and maintained the reaction temperature at 50° C. for three hours. The total monomer consumed was 9.0 moles. The vented product weighted 1013 grams. The product was distilled to recover 150 grams of liquid boiling in the range 210°-213° C. with a refractive index of 1.4447 and a density of 0.78 grams per cc. at 25° C. This product was made up of oligomers of three to five mers.

I claim:

1. A method of olefin oligomerization consisting essentially of
   (1) mixing a combination catalyst consisting essentially of the reaction product of (A) a nickel bis-diorgano-orthophosphate of the general formula Ni[OP(O)(OR)$_2$]$_2$ in which each R is selected from the group consisting of non-aromatic hydrocarbon groups free of aliphatic unsaturation and containing one to eight carbon atoms, non-aromatic hydrocarbon ether groups free of aliphatic unsaturation and containing three to six carbon atoms, and chlorinated and brominated derivatives thereof and (B) an alkyl aluminum halide of the general formula R'$_c$AL X$_d$ in which each R' is an alkyl group of one to six carbon atoms, each X is a halogen atom, each of $c$ and $d$ is 1 or 2 and the total of $c$ and $d$ is 3, the mol ratio of (A) to (B) ranging from 1:1 to 1:20, with (D) an olefinic hydrocarbon containing no more than about 8 carbon atoms, the mol ratio of total catalyst to component (D) ranging from 0.0001:1 to 0.01:1, at a temperature and pressure and for a time sufficient to cause reaction of (D); and
   (2) separately the resulting products.

2. A method in accordance with claim 1 wherein said catalyst components (A) and (B) and said olefinic hydrocarbon (D) are further mixed with (E) a hydrocarbon solvent free of aliphatic unsaturation and containing up to 14 carbon atoms.

3. A method in accordance with claim 2 wherein component (D) is selected from the class consisting of aliphatic hydrocarbons containing two to four carbon atoms and styrene.

4. A method in accordance with claim 2 wherein said hydrocarbon solvent (E) is an aromatic hydrocarbon substituted with up to about four non-interfering substituents.

5. A method for olefin polymerization consisting essentially of
   (1) mixing a combination catalyst for olefin polymerization consisting essentially of the reaction product of (A) a nickel bis-diorgano-orthophosphate of the general formula: Ni[OP(O)(OR)$_2$]$_2$ in which each R is selected from the group consisting of non-aromatic hydrocarbon groups free of aliphatic unsaturation and containing one to eight carbon atoms, non-aromatic hydrocarbon ether groups free of aliphatic saturation and containing three to six carbon atoms, and chlorinated and brominated derivatives thereof, (B) an alkyl aluminum halide of the general formula R'$_c$Al X$_d$ in which each R' is an alkyl group of one to six carbon atoms, each X is a halogen atom, each of $c$ and $d$ is 1 or 2 and the total of $c$ and $d$ is 3, the mol ratio of (A) to (B) ranging from 1:1 to 1:20 and (C) a vanadium bis-diorgano-orthophosphate of the general formula V(O)[OP(O)(OR)$_2$]$_2$ in which each R is as defined above, the mol ratio of (C) to (B) ranging from 1:4 to 1:10, with (D) an olefinic hydrocarbon containing no more than about eight carbon atoms, the mol ratio of total catalyst to component (D) ranging from 0.0001:1 to 0.01:1, at a temperature and pressure and for a time sufficient to cause reaction of (D); and (2) separating the resulting products.

6. A method in accordance with claim 5 wherein said combination catalyst of components (A) (B) and (C) and said olefinic hydrocarbon (D) are also mixed with (E) a hydrocarbon solvent free of aliphatic unsaturation and containing up to 14 carbon atoms.

7. A method in accordance with claim 6 wherein component (D) is selected from the class consisting of aliphatic hydrocarbons containing two to four carbon atoms and styrene.

8. A method in accordance with claim 6 wherein said hydrocarbon solvent (E) is an aromatic hydrocarbon substituted with up to about four non-interfering substituents.

* * * * *